United States Patent [19]

Morgan et al.

[11] 4,048,218
[45] Sept. 13, 1977

[54] FLAME RETARDANT MERCAPTOCARBOXYLIC ACID ESTERS OF HALOGENATED AROMATIC POLYOLS

[75] Inventors: Charles R. Morgan, Brookeville; David E. Kramm, Laurel, both of Md.

[73] Assignee: W. R. Grace & Co., New York, N.Y.

[21] Appl. No.: 552,674

[22] Filed: Feb. 24, 1975

[51] Int. Cl.$^2$ ............... C07C 149/20; C07C 149/22
[52] U.S. Cl. .................... 560/147; 204/159.22; 260/2.5 BB; 260/47 UA; 260/77.5 AM; 260/77.5 AT; 260/77.5 AP; 260/79.5 C; 260/399; 560/17; 560/121; 560/123; 260/830 P; 260/853; 260/859 PV; 560/124; 560/125
[58] Field of Search .................... 260/481 R, 399

[56] References Cited
PUBLICATIONS

Chem. Abstracts, 59:15445c, (1963).
Chem. Abstracts, 74:54500j, (1971).
Chem. Abstracts, 59:7721f, (1963).
Chem. Abstracts, 67:100575t.

Primary Examiner—Vivian Garner
Attorney, Agent, or Firm—Richard P. Plunkett; K. E. Prince

[57] ABSTRACT

This invention is directed to novel halogen-containing polythiols which impart improved flame retardancy to radiation cured thiol-ene compositions.

2 Claims, No Drawings

FLAME RETARDANT MERCAPTOCARBOXYLIC ACID ESTERS OF HALOGENATED AROMATIC POLYOLS

This invention is directed to flame retardant polythiols and cured compositions therefrom which can be used as coatings to impart flame retardancy to the substrates.

Many areas including the building industry and the electrical industry have stepped up their search for improved fire retardant materials which when used as coatings would allow the use of known materials, e.g. high organic polymers, wood, etc., as products which do not presently meet fire retardant standards set out in the building or electrical code.

Curable compositions of polyene and polythiol are well known in the art. See U.S. Pat. Nos. 3,661,744 and 3,535,193. Said polyene/polythiol compositions, although they readily form coatings on exposure to U.V. or high energy ionizing radiation, the flame retardancy of the cured polythioether material leaves something to be desired.

One object of the instant invention is to produce novel halogen-containing polythiols. Another object of the instant invention is to produce a composition of halogen-containing polythiols and a polyene which upon curing, e.g. by U.V. or high energy ionizing radiation as a coating on a substrate imparts improved flame retardancy thereto. Other objects will become apparent from a reading hereinafter.

In accord with fulfilling these objects, one aspect of this invention resides in the formation of novel halogen-containing polythiols of the formula:

wherein R is a member of the group consisting of

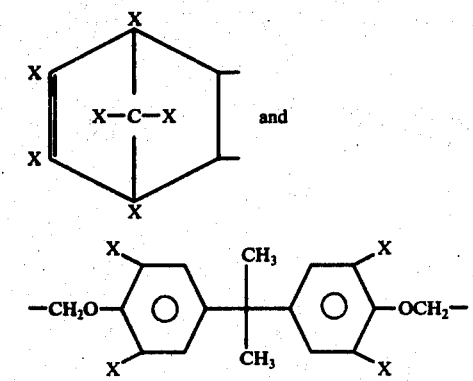

X is a halogen selected from the group consisting of Cl and Br and $R_1$ is a polyvalent organic radical member free of reactive carbon to carbon unsaturation containing members of the group consisting of aryl, substituted aryl, aralkyl, substituted aralkyl, cycloalkyl, substituted cycloalkyl, alkyl and substituted alkyl groups containing 1 to 16 carbon atoms and mixtures thereof.

Preferred examples of operable aryl members are either phenyl or naphthyl, and of operable cycloalkyl members which have from 3 to 8 carbon atoms. Likewise, preferred substitutents on the substituted members may be such groups as chloro, bromo, nitro, acetoxy, acetamido, phenyl, benzyl, alkyl, and alkoxy of 1 to 9 carbon atoms, and cycloalkyl of 3 to 8 carbon atoms.

Operable mercaptocarboxylic acids include but are not limited to thioglycollic acid (mercaptoacetic acid), α-mercaptopropionic acid, β-mercaptopropionic acid, 4-mercaptobutyric acid, mercaptovaleric acids, mercaptoundecylic acid, mercaptostearic acid and o- and p-mercaptobenzoic acids. Preferably, thioglycollic or β-mercaptopropionic acid is employed. Mixtures of various mercaptocarboxylic acids are operable as well.

The polythiol esters are prepared by the esterification of the appropriate halogen-containing polyol with mercaptocarboxylic acid in the presence of an acid catalyst, the water formed during the reaction being removed as an azeotrope in a suitable solvent.

The reaction is carried out at atmospheric pressure at a temperature in the range of from 60° to about 150° C, preferably from 60° to 110° C for a period of 30 minutes to about 24 hours.

Suitable acid catalysts include but are not imited to p-toluenesulfonic acid, sulfuric acid, hydrochloric acid and the like. Useful inert solvents include but are not limited to saturated aliphatic hydrocarbons, aromatic hydrocarbons, chlorinated hydrocarbons, ethers, ketones, etc. Representative nonlimiting examples of solvents include toluene, benzene, xylene, chloroform, 1,2-dichloroethane, etc.

The aforesaid halogen-containing polythiols can be compounded with polyenes and upon curing results in a cured polythioether material having improved flame retardancy.

The mole ratio of ene/thiol groups for preparing the curable composition is from about 1/0.25 to about 1/4.0 and desirably about 1/0.75 about 1/1.25 group ratio.

Generally stated, the present invention provides a curable composition which comprises a polyene component and a flame retardant polythiol component. A photosensitizer is added when curing is by U.V. light. The polyene component cured by the flame retardant polythiols of the instant invention is known in the art and is set out in U.S. Pat. No. 3,661,744 and 3,535,193, both assigned to the same assignee of this appliction and incorporated herein by reference.

The polyene component may be represented by the formula:

wherein m is an integer of at least 3, wherein X is a member selected from the group consisting of:

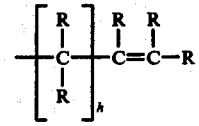 (a)

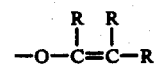 (b)

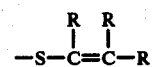 (c)

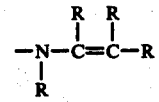 (d)

-continued

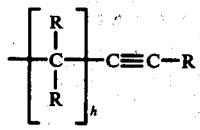

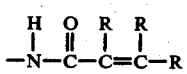

In the groups (a) to (g), $h$ is an integer from 1 to 9; R is a radical selected from the group consisting of hydrogen, fluorine, chlorine, furyl, thienyl, pyridyl, phenyl, and substituted phenyl, benzyl and substituted benzyl, alkyl and substituted alkyl, alkoxy and substituted alkoxy, and cycloalkyl and substituted cycloalkyl. The substituents on the substituted members are selected from the group consisting of nitro, chloro, fluoro, acetoxy, acetamide, phenyl, benzyl, alkyl, alkoxy and cycloalkyl. Alkyl and alkoxy have from one to nine carbon atoms and cycloalkyl has from 3 to 8 carbon atoms.

The members (a) to (g) are connected to [A] through divalent chemically compatible derivative members. The members (a) to (g) may be connected to [A] through a divalent chemically compatible derivative member of the group consisting of $Si(R)_2$, carbonate, carboxylate, sulfone,

alkyl and substituted alkyl, cycloalkyl and substituted cycloalkyl, urethane and substituted urethane, urea and substituted urea, amide and substituted amide, amine and substituted amine, and aryl and substituted aryl. The alkyl members have from one to nine carbon atoms, the aryl members are either phenyl or naphthyl, and the cycloalkyl members have from three to eight carbon atoms with R and said members substituted being defined above. B is a member of the group consisting —O—, —S—, and —NR—.

The member [A] is polyvalent; free of reactive carbon-to-carbon unsaturation, free of highly water-sensitive members; and consisting of atoms selected from the group consisting of carbon, oxygen, nitrogen, chlorine, bromine, fluorine, phosphorus, silicon and hydrogen. Said atoms are combined to form chemically compatible members of the group consisting of carbonate, carboxylate, carbonyl, ether, silane, silicate, phosphonate, phosphite, phosphate, alkyl and substituted alkyl, cycloalkyl and substituted cycloalkyl, aryl and substituted aryl, urethane and substituted urethane, urea and substituted urea, amine and substituted amine, amide and substituted amide, hydroxyl, heterocyclic carbon containing radical, and mixtures thereof; said substituents on said members being defined above.

The polyene component has a molecular weight in the rage from about 64 20,000, preferably about 200 to about 10,000; and a viscosity in the range from essentially 0 to 20 million centipoises at 70° C. as measured by a Brookfield Viscometer.

The member [A] of the polyene composition may be formed primarily of alkyl radicals, phenyl and urethane derivatives, oxygenated radicals, and nitrogen substituted radicals. The member [A] may also be represented by the formula:

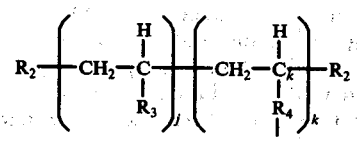

wherein $j$ and $k$ are integers greater than 1; $R_2$ is a member of the group consisting of hydrogen, and alkyl having one to nine carbon atoms; $R_3$ is a member of the group consisting of hydrogen, and saturated alkyl having 1 to 9 carbon atoms; $R_4$ is a divalent derivative of the group consisting of phenyl, benzyl, alkyl, cycloalkyl, substituted phenyl, substituted benzyl, substituted alkyl and substituted cycloalkyl; with the terms alkyl, cycloalkyl and members substituted being defined above.

General representative formulas for the polyenes of the present invention may be prepared as exemplified below:

I. Poly (alkylene-ether) Polyol Reacted with Unsaturated Monoisocyanates Forming Polyurethane Polyenes and Related Polymers Trifunctional

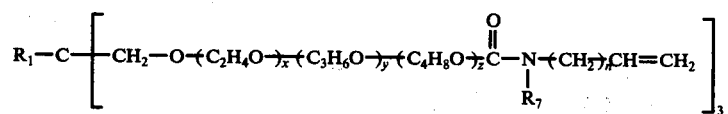

Tetrafunctional

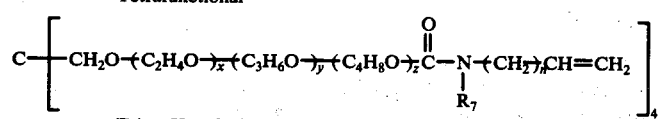

Tri-to-Hexafunctional

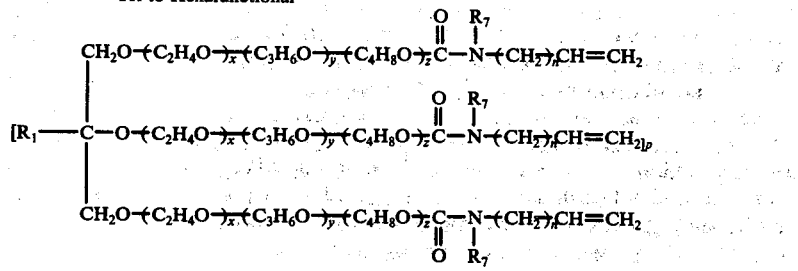

-continued

Interconnected-Modified Tetrafunctional

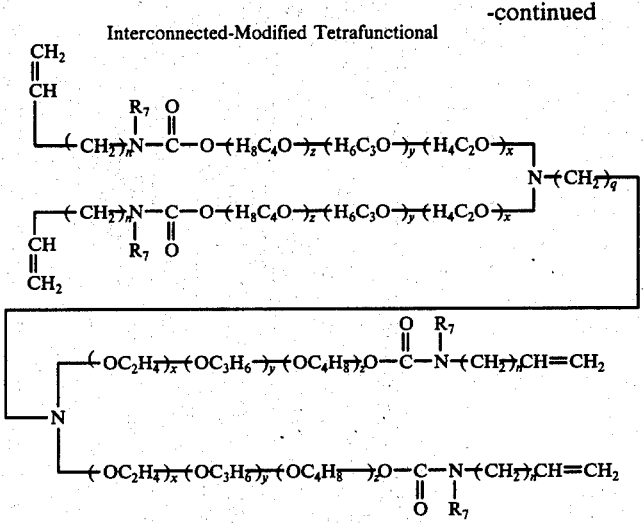

II. Poly (alkylene-ether)Polyol Reacted with Polyisocyanate and Unsaturated Monoalcohol Forming Polyurethane Polyenes and Related Polymers

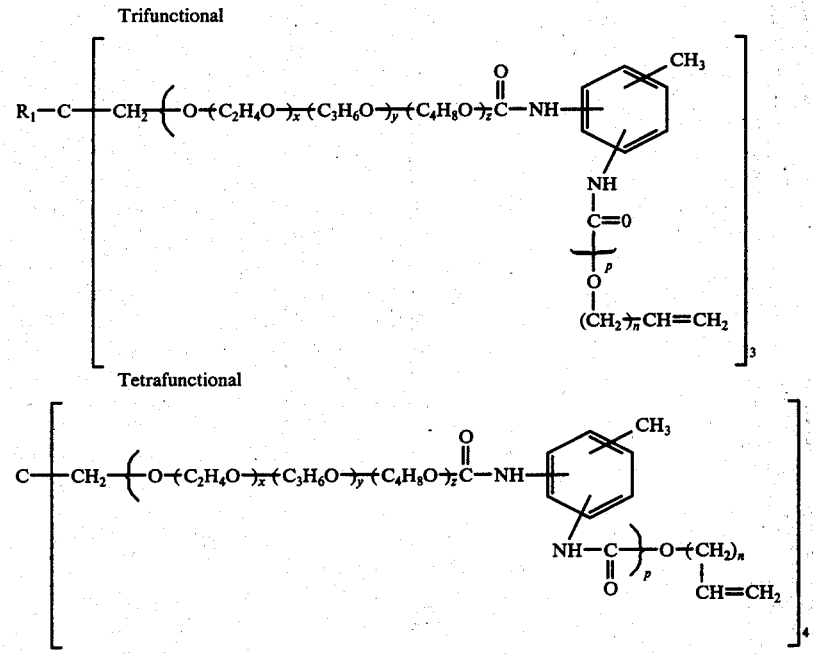

In the above formulas, the sum of $x + y + z$ in each chain segment is at least 1; $p$ is an integer of 1 or more; $q$ is at least 2; $n$ is at least 1; $R_1$ is selected from the group consisting of hydrogen, phenyl, benzyl, alkyl, cycloalkyl, and substituted phenyl; and $R_7$ is a member of the group consisting of $CH_2=CH-(CH_2-)_n$, hydrogen, phenyl, cycloalkyl, and alkyl.

The novel class of polyenes of this invention derived from carbon to carbon unsaturated monoisocyanates may be characterized by extreme ease and versatility of manufacture when the liquid functionality desired is greater than about three. For example, consider an attempted synthesis of a polyhexene starting with an —OH terminated polyalkylene ether hexol such as "Niax" Hexol LS-490 (Union Carbide Corp.) having a molecular weight of approximately 700, and a viscosity of 18,720 cps at 20° C. An attempt to terminate this polymer with ene groups by reacting 1 mole of hexol with 6 moles of tolylene diisocyanate (mixed-2,4-, 2,6-isomer product) and 6 moles of allyl alcohol proceeded nicely but resulted in a prematurely chain extended and crosslinked solid product rather than an intended liquid polyhexene. Using the monoisocyanate route, however, this premature chain extension may be avoided and the desired polyurethane-containing liquid polyhexene may be very easily prepared by a simple, one-step reaction of one mole of hexol with 6 moles of allyl isocyanate. This latter polyhexene has the added advantage of being cured using the teachings of this invention to a non-yellowing polythioether polyurethane product. Similarly, the unsaturated monoisocyanate technique may be used to prepare liquid polyenes from other analagous highly functional polyols such as cellulose, polyvinyl alcohol, partially hydrolized polyvinyl acetate, and the like, and highly functional polyamines such as tetraethylene pentamine, polyethyleneimine, and the like.

A general method of forming one type of polyene containing urethane groups is to react a polyol of the general formula $R_{11}\text{---(OH)}_n$ wherein $R_{11}$ is a polyvalent organic moiety free from reactive carbon-to-carbon unsaturation and $n$ is at least 2; with a polyisocyanate of the general formula $R_{12}\text{---(NCO)}_n$ wherein $R_{12}$ is a polyvalent organic moiety free from reactive carbon-to-carbon unsaturation and $n$ is at least 2 and a member of the group consisting of an ene-ol, yne-ol, ene-amine and yne amine. The reaction is carried out in an inert moisture-free atmosphere (nitrogen blanket) at atmospheric pressure at a temperature in the range from 0° to about 120° C for a period of about 5 minutes to about 25 hours. In the case where an ene-ol or yne-ol is employed, the reaction is preferably a one step reaction wherein all the reactants are charged together. In the case where an ene-amine or yne-amine is used, the reaction is preferably a two step reaction wherein the polyol and the polyisocyanate are reacted together and thereafter preferably at room temperature, the ene-amine or yne-amine is added to the NCO terminated polymer formed. The group consisting of ene-ol, yne-ol, ene-amine and yne-amine are usually added to the reaction in an amount such that there is one carbon-to-carbon unsaturation in the group member per hydroxyl group in the polyol and said polyol and group member are added in combination in a stoichiometric amount necessary to react with the isocyanate groups in the polyisocyanate.

A second general method of forming a polyene containing urethane groups (or urea groups) is to react a polyol (or polyamine) with an ene-isocyanate or an yne-isocyanate to form the corresponding polyene. The general procedure and stoichiometry of this synthesis route is similar to that described for polyisocyanates in the preceding. In this instance, a polyol reacts with an ene-isocyanate to form the corresponding polyene. It is found, however, that products derived from this route, when cured in the presence of an active light source and a polythiol, may form relatively weak solid polythioether products. To obtain stronger cured products, it is desirable to provide polar functional groupings within the main chain backbone of the polymeric polyene. These polar functional groupings serve as connecting linkages between multiple repeating units in the main chain series, and serve as internal strength-reinforcing agents by virtue of their ability to create strong inter-chain attraction forces between molecules of polymer in the final cured composition.

Another group of polyenes operable in this invention includes those polyenes in which the reactive unsaturated carbon to carbon bonds are conjugated with adjacent unsaturated groupings. Examples of operable reactive conjugated ene systems include, but are not limited to the following:

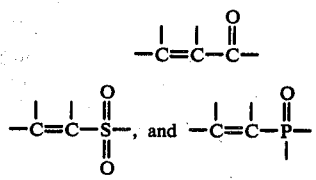

A few typical examples of polyenes which contain conjugated reactive double bonds groupings such as those described above are the triacrylate of the reaction product of trimethylolpropane with 20 moles of ethylene oxide, pentaetythritol tetraacrylate, trimethylolpropane trimethacrylate and triacrylate, triacrylate of isocyanurate, tetramethacrylate, and the like.

The aforesaid polyenes containing ester groups may be formed by reacting an acid of the formula $R_{13}\text{---(COOH)}_n$ wherein $R_{13}$ is a polyvalent organic moiety free from reactive carbon-to-carbon unsaturation and $n$ is at least 3, with either an ene-ol or yne-ol. The reaction is carried out at atmospheric pressure at a temperature in the range from 0° to about 120° C. for a period of 5 minutes to 25 hours. Usually the reaction is carried out in the presence of a catalyst (p-toluene sulfonic acid) and in the presence of a solvent, e.g. benzene at refluxing temperature. The water formed is azeotroped off of the reaction.

Another method of making an ester containing polyene is to react a polyol of the formula $R_{11}\text{---(OH)}_n$ wherein $R_{11}$ is a polyvalent organic moiety free from reactive carbon-to-carbon unsaturation and $n$ is at least 3; with ether an ene-acid or an yne-acid. The reaction is carried out in the same manner as set out above for the ester-containing polyenes.

A further group of polyenes which are operable in the present invention includes unsaturated polymers in which the double or triple bonds occur also within the main chain of molecules. These are derived primarily from standard diene monomers such as polyisoprene, butadiene, styrene-butadiene rubber, isobutylene-isoprene rubber, polychloroprene, styrene-butadiene-acrylonitrile rubber and the like unsaturated polyesters, polyamides, and polyurethanes derived from monomers containing "reactive" unsaturation. As examples, adipic acid-butenediol, 1,6-hexanediamine-fumaric acid and 2,4-tolylene diisocyanate-butenediol condensation polymers and the like are operable.

In forming the polyenes of the present invention, catalytic amounts of a catalyst may be employed to speed up the reaction. This is especially true in the case where an ene-ol is used to form the polyene. Such catalysts are well known to those in the art and include organometallic compounds such as stannous octoate, stannous oleate, dibutyl tin dilaurate, cobalt acetylacetonate, ferric acetylacetonate, lead naphthanate and dibutyl tin diacetate. The polyene/polythiol mole ratios are selected so as to provide a solid, self-supporting cured product under ambient conditions in the presence of actinic or high energy ionizing radiation.

The curing reaction can be initiated by either U.V. radiation or high energy ionizing radiation. The U.V. radiation can be obtained from sunlight or special light sources which emit significant amounts of U.V. light having a wavelength in the range of about 2,000 to 4,000 Angstrom units. When U.V. radiation is used for the curing reaction, a dose of 0.0004 to 60 watts/centimeter$^2$ is employed.

When U.V. radiation is used for curing, a photosensitizer is added to the composition. Preferred photocuring rate accelerators or photosensitizers are the aldehyde and ketone carbonyl compounds having at least one aromatic nucleus attached directly to the

group. Various photosensitizers include, but are not limited to, benzophenone, acetophenone, o-methoxybenzophenone, acenapthenequinone, methyl ethyl ketone, valerophenone, hexanophenone, γ-phenylbutyrophenone, p-morpholinopropiophenone, dibenzosuberone, 4-morpholinobenzophenone, 4'-morpholinodeoxybenzoin, p-diacetylbenzene, 4-aminobenzophenone, 4'-methoxyacetophenone, benzaldehyde, α-tetralone, 9-acetylphenanthrene, 2-aceytlphenanthrene, 10-thioxanthenone, 3-acetylphenanthrene, 3-acetylindole, 9-fluorenone, 1-indanone, 1,3,5-triacetylbenzene, thioxanthen-9-one, xanthene-9-one, 7-H-benz[de]anthracen-7-one, 1-naphthaldehyde, 4,4'-bis(dimethylamino) benzophenone, fluorene-9-one, 1'-acetonaphthone, 2'-acetonaphthone, 2,3-butanedione, triphenylphosphine, tri-o-tolyphosphine, acetonaphthone, 2,3-butanedione, benz[a]anthracene 7,12 dione, etc. which serve to give greatly reduced exposure times and thereby when used in conjunction with various forms of energetic radiation yield very rapid, commercially practical time cycles by the practice of the instant invention. The photosensitizers are usually added in an amount ranging from 0.0005 to 50% by weight.

The radiation curable compositions of the instant invention can also be cured by high energy ionizing irradiation. A preferred feature of the ionizing irradiation operation of the instant invention is treatment with high energy particle irradiation or by gamma-rays or X-rays. Irradiation employing particles in the instant invention includes the use of positive ions, (e.g., protons, alpha particles and deuterons), electrons or neutrons. The charged particles may be accelerated to high speeds by means of various voltage gradient mechanisms such as a Van de Graaff generator, a cyclotron, a Cockroft Walton accelerator, a resonant cavity accelerator, a betatron, a G.E. resonant transformer, a synchrotron or the like. Furthermore, particle irradiation may also be supplied from radioactive isotopes or an atomic pile. Gamma rays or X-rays may be obtained from radioisotopes (e.g. cobalt 60) or by particle bombardment of suitable target material (e.g., high energy electrons on a gold metal target).

The dose rate for the irradiation operable to cure the coating in the instant invention is in the range 0.00001 to 1000 megarads/second.

The amount of ionizing radiation which is employed in curing the radiation curable material in the instant invention can vary between broad limits. Radiation dosages of less than a megarad up to 10 megarads or more for electrons are operable, preferably 0.02 to 5 megarads energy absorbed are employed. For gamma-rays or X-rays, radiation dosages in the range 0.0001 to 5.0 megarads energy absorbed are operable. The irradiation step is ordinarily performed under ambient temperature conditions but can be performed at temperatures ranging from below room temperature up to temperatures of 90° C.

The compositions to be radiation cured, i.e., converted to solid coatings, in accord with the present invention may, if desired, include such additives as antioxidants, inhibitors, activators, fillers, pigments, dyes, antistatic agents, flame-retardant agents, thickeners, thixotropic agents, surface-active agents, viscosity modifiers, plasticizers, and the like within the scope of this invention. Such additives generally are preblended with the polyene or polythiol prior to coating it on the substrate. The aforesaid additives may be present in quantities up to 500 parts or more per 100 parts radiation curable compositions by weight and preferbly 0.0005 to 300 parts on the same basis. The type and concentration of the additives must be selected with care so that the final composition remains radiation curable under conditions of exposure.

The curable liquid polymer compositions of the instant invention prior to curing can be pumped, poured, brushed, sprayed, doctored, rolled, trowelled, dipped-coated, extruded or gunned into place into cavities, into molds, or onto vertical or horizontal flat surfaces in a uniform fashion. Following such application curing in place to a solid resin or an elastomer can be made to occur very rapidly. The compositions can be applied to various substrates and adhere well to glass, wood, metals, concrete, certain plastics, paints, enamels, fabrics, paper, paper board, porcelain, ceramics, brick, cinder block, plaster and vinyl floor tile.

The liquid polyethioether-forming components and compositions of the instant invention can, prior to curing, be admixed with or blended with other monomeric and polymeric materials such as thermoplastic resins, elastomers or thermosetting resin monomeric or polymeric compositions. The resulting blend can be subjected to conditions for curing or co-curing of the various components of the blend to give cured products having unusual physical properties. Examples of the classes of the materials which can be admixed, blended or co-cured with the polythiolether-forming compositions of the instant invention are illustrated by, but not limited to, the following: epoxy resins, phenolic resins, polysulfide resins, and elastomers, polyurethane resins and elastomers, polyamide resins, polyvinylchloride resins, amphorous or crystalline polyolefins, polyacrylonitrile polymers, silicone polymers, urea-formaldehyde resins, polyether resins and elastomers and the like.

The solid cured polythioether polymer products resulting from the instant invention have many and varied uses. Examples of some uses include but are not limited to adhesives; caulks; elastomeric sealants, coatings, such as wire coatings, electrical circuits cover resists, photoresists and the like, encapsulating or potting compounds, liquid castable elastomers; thermoset resins, impregnants for fabric, cloth, fibrous webs and other porous substrates; laminating adhesives and coatings; mastics; glazing compounds; fiberglass reinforced composites; sizing or surface finishing agents, filleting compounds; cured in place gasketing compounds; rocket fuel binders; foamable thermosetting resins or elastomers; molded articles such a gaskets, diaphragms, ballons, automobile tires, etc.

The molecular weight of the polyenes of the present invention may be measured by various conventional methods including solution viscosity, osmotic pressure and gel permeation chromatography. Additionally, the molecular weight may be calculated from the known molecular weight of the reactants.

The viscosity of the polyenes and polythiols may be measured on a Brookfiled Viscometer at 30° or 70° C in accord with the instructions therefor.

The components to be cured may be prepared as either single-packaged or multi-packaged liquid polymer systems which may be cured to solid polythioether elastomers without liberating gaseous by-products which cause bubbles and voids in the vulcanizate. Thus, there is provided curable liquid polymer systems composed of polyenes and polythiols in which the components individually are storage stable and which are not sensitive to or deteriorated by traces of moisture or oxygen containing gas such as may be encountered during normal storage or handling procedures. Solid resinous or elastomeric products may be prepared from flowable liquid in a system in which the rate of curing may be inhibited or retarded by the use of chemical inhibitors, antioxidants, and the like. Conventional curing inhibitors or retarders which may be used in order to stabilize the components or curable compositions so as to prevent premature onset of curing may include certain acids and bases; hydroquinone; p-tert-butyl catechol; 2,6-di-tert-butyl-p-methylphenol; phenothiazine; N-phenyl-2-naphthylamine; pyrogallol; octadecyl-β-(4-hydroxy-3,5-di-t-butyl phenyl)-propionate; and the like. The cured product maybe characterized as in the thermally and oxidatively stable state since there is no reactive carbon-to-carbon unsaturation in the main backbone chain.

As used herein the term polyene and the term polyne refers to single or complex species of alkenes or alkynes having a multiplicity of terminal reactive carbon-to-carbon unsaturated functional groups per average molecule. For example, a diene is a polyene that has two reactive carbon-to-carbon double bonds per average molecule. Combinations of reactive double bonds and reactive triple bonds within the same molecule are also possible such as for monovinylacetylene which is a polyeneyne under this definition. For purposes of brevity all these classes of compounds are referred to hereafter as polyenes.

In defining the position of the reactive functional carbon-to-carbon unsaturation, the term terminal is intended to mean that functional unsaturation is at an end of the main chain in the molecule; whereas by near terminal is intended to mean that the functional unsaturation is not more than 10 carbon atoms and typically less than eight carbon atoms from an end of the main chain in the molecule. The term pendant means that the reactive carbon-to-carbon unsaturation is located terminal or near-terminal in a branch of the main chain as contrasted to a position at or near the ends of the main chain. For purposes of brevity all of these positions are referred to herein generally as terminal unsaturation.

Functionality as used herein refers to the average number of ene or thiol groups per molecule in the polyene or polythiol, respectively. For example a triene is a polyene with an average of three reactive carbon-to-carbon unsaturated groups per molecule and thus has a functionality (f) of three. A dithiol is a polythiol with an average of two thiol groups per molecule and thus has a functionality (f) of two. Since the polythiols of the instant invention have a functionality of 2, it is necessary in order to obtain a cured polythioether product that the polyene have a functionality of at least 3.

The following examples will aid in explaining but expressly not limit the instant invention. Unless otherwise noted all parts and percentages are by weight.

The Oxygen Index herein was measured in accord with the procedures set out in ASTMD-2963 using 20 mil thick samples

PREPARATION OF FLAME RETARDANT POLYTHIOLS

EXAMPLE I 180.5 g of 1,4,5,6,7,7-Hexachloro-5-norbornene-2,3-dimethanol (Hooker Het Diol®), and 111.3 g of β-mercaptopropionic acid along with 500 ml of dichloroethane as solvent and 9.64 g of p-toluene-sulfonic acid as catalyst were charged into a 1-liter flask equipped with a stirrer, thermometer and reverse Dean Stark trap The mixture was heated to reflux. Water of esterification was removed by azeotropic distillation. The amount of water collected was about 15 ml in 6.5 hours. The reaction solution was cooled to room temperature and washed once with 500 ml of water, two times with 500 ml portions of 5% sodium bicarbonate solution, and then one time with 500 ml of water. The resulting dichloroethane solution containing the product was dried over 40 g of magnesium sulfate, treated with 1 g of Norit A decolorizing carbon, and then filtered. After filtration, the solvent was removed by vacuum stripping to give 161 g of a polythiol of the formula:

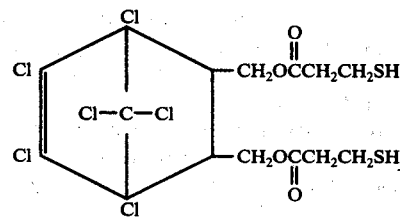

with a thiol content of 3.66 meq/g (Theory=3.72 meq/g). This polythiol will hereinafter be referred to as Polythiol I.

EXAMPLE II 948 g of the bis(2-hydroxyethyl) ether) of tetrabromobisphenol A (Great Lakes Chemical Corporation BA-50™), 349.5 g of β-mercaptopropionic acid, 1200 ml of dichloroethane as solvent, and 26 g of p-toluene-sulfonic acid as catalyst were charged into a reaction flask equipped with a stirrer, thermometer, and a reverse Dean Stark trap. The mixture was heated to reflux and the water of esterification removed by azeotropic distillation. The amount of water collected was about 61 ml in 3.5 hours. The reaction solution was cooled to room temperature and washed once with 1800 ml of water. The resulting dichloroethane solution containing the product was dried over 120 g of magnesium sulfate, treated with 1 g of Norit A decolorizing carbon, and then filtered. After filtration, the solvent was removed by vacuum stripping to give 932 g of a polythiol of the formula:

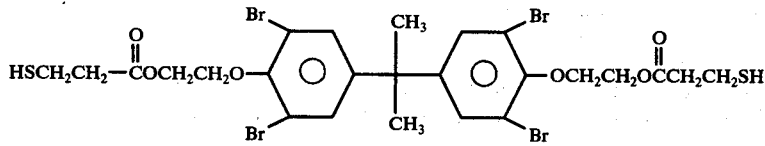

with a thiol content of 2.46 meq/g (Theory=2.48 meq/g). This polythiol will hereinafter be referred to as Polythiol II.

The following example shows the improved flame retardancy obtained with halogen-containing polythiols of the invention herein as compared with commercially available polythiol.

EXAMPLE III

The following compositions were compounded by admixing the ingredients with stirring until a homogeneous admixture was obtained.

| Composition A | |
|---|---|
| Triallylcyanurate | 1610 g |
| Pentaerythritol Tetrakis (Mercaptopropionate) | 2390 g |
| Benzophenone | 0.8 g |
| Phosphorous acid | 80 g |
| Hydroquinone | .2 g |
| Pyrogallol | .2 g |
| Composition B | |
| Triallylcyanurate | 23 g |
| Polythiol I | 76.7 g |
| Benzophenone | .2 g |
| Phosphorous acid | .02 g |
| Hydroquinone | .005 g |
| Pyrogallol | .005 g |
| Composition C | |
| Triallylcyanurate | 24.8 g |
| Polythiol II | 115.2 g |
| Benzophenone | 2.8 g |
| Phosphorous acid | .07 g |
| 2,6-di-tert-butyl-4-methyl phenol commercially available under the tradename "Ionol" from Shell Chemical Company | .14 g |
| octadecyl-β-(4-hydroxy-3,5-di-t-butyl phenyl)-propionate - commercially available from Geigy-Ciba under the tradename "IRGANOX 1076" | .28 g |

Thereafter the viscous admixtures were then poured onto a mylar backing sheet and drawn down to a uniform thickness of 20 mils. The coatings were then exposed to a mercury vapor lamp for one minute at a surface intensity on the coatings of 10,000 microwatts/cm². The cured coatings were removed from the mylar sheet, cut to the proper dimensions and measured for oxygen indexes. The results of the oxygen indexes were as follows:

| Composition | Oxygen Index (%) |
|---|---|
| A | 21.0 |
| B | 28.9 |
| C | 30.2 |

From this Oxygen Index data it can be seen that the halogen-containing polythiols of Compositions B and C significantly improve flame retardancy as measured by the increased oxygen index of the cured polyene/polythiol compositions.

What is claimed is:

1. As a composition of matter, a halogen-containing polythiol of the formula

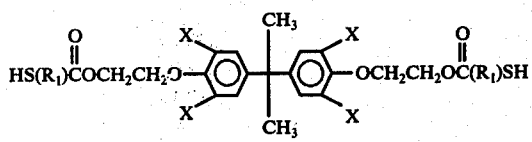

wherein X is a halogen selected from the group consisting of Cl and Br, and $R_1$ is an alkyl group containing 1-16 carbon atoms.

2. As a composition of matter

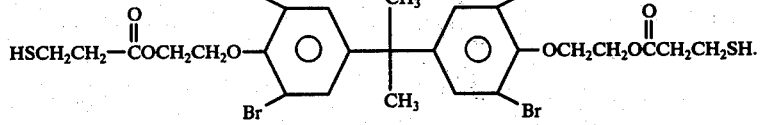

* * * * *